United States Patent
Ramakrishna et al.

(10) Patent No.: US 7,507,561 B2
(45) Date of Patent: Mar. 24, 2009

(54) PROCESS FOR THE PRODUCTION OF POLYLACTIC ACID (PLA) FROM RENEWABLE FEEDSTOCKS

(75) Inventors: Sonti Venkata Ramakrishna, Navi Mumbai (IN); Vidhya Rangaswamy, Navi Mumbai (IN); Dharmendra Jain, Navi Mumbai (IN); Raj Kumar Jagdambalal, Vadodara (IN); Pradip Shantibhai Patel, Vadodara (IN); Debojyoti Kar, Vadodara (IN); Subramania Ramachandran, Vadodara (IN); Pralhad Ambadas Ganeshpure, Vadodara (IN); Uma Sankar Satpathy, Vadodara (IN)

(73) Assignee: Reliance Life Sciences Pvt. Ltd., Maharashtra (IN)

( * ) Notice: Subject to any disclaimer, the term of this patent is extended or adjusted under 35 U.S.C. 154(b) by 172 days.

(21) Appl. No.: 11/132,991

(22) Filed: May 19, 2005

(65) Prior Publication Data
US 2006/0036062 A1    Feb. 16, 2006

(30) Foreign Application Priority Data
May 20, 2004 (IN) .................... 576/MUM/2004

(51) Int. Cl.
*C12P 7/62* (2006.01)

(52) U.S. Cl. .................................................... 435/135

(58) Field of Classification Search ................ 435/135; 528/354
See application file for complete search history.

(56) References Cited

U.S. PATENT DOCUMENTS

| 5,310,865 | A | | 5/1994 | Enomoto et al. | |
|---|---|---|---|---|---|
| 5,369,122 | A | * | 11/1994 | Steinmetzer | 514/423 |
| 5,508,378 | A | * | 4/1996 | Ohara et al. | 528/354 |
| 5,770,682 | A | * | 6/1998 | Ohara et al. | 528/354 |
| 6,060,622 | A | * | 5/2000 | Okuyama et al. | 562/589 |
| 6,326,458 | B1 | | 12/2001 | Gruber et al. | |
| 6,472,559 | B2 | | 10/2002 | Baniel et al. | |
| 6,569,989 | B2 | | 5/2003 | Ohara et al. | |
| 7,238,837 | B1 | * | 7/2007 | Eyal et al. | 562/589 |

FOREIGN PATENT DOCUMENTS

| EP | 0 790 229 | | 8/1997 |
|---|---|---|---|
| WO | WO2004057008 | * | 7/2004 |

\* cited by examiner

*Primary Examiner*—Herbert J. Lilling
(74) *Attorney, Agent, or Firm*—J. Harold Nissen; Lackenbach Siegel, LLP

(57) ABSTRACT

The present invention relates to an efficient process for producing polylactic acid from fermentation of renewable agricultural feed-stocks not limited to molasses or cane bagasse employed as starting material. The present invention in particular provides a cost effective and industrially scalable process for producing polylactic acid obtained by fermentation of Lactic acid having industrial applications.

27 Claims, 1 Drawing Sheet

PROCESS FOR THE PRODUCTION OF POLYLACTIC ACID (PLA) FROM RENEWABLE FEEDSTOCKS

CROSS REFERENCE TO RELATED APPLICATION

This application claims priority from provisional Indian provisional patent application filed May 20, 2004, under Application No.576/MUM/2004.

FIELD OF INVENTION

The present invention relates to an efficient process for producing polylactic acid from fermentation of renewable agricultural feed-stocks not limited to molasses or cane bagasse employed as starting material. The present invention in particular provides a cost effective and industrially scalable process for producing polylactic acid obtained by fermentation of Lactic acid having industrial applications.

BACKGROUND OF INVENTION

Lactic acid fermentation has been gaining increased attention in the recent years primarily due to its importance as a building block in the manufacture of biodegradable plastics. Lactic acid can be produced from various substrates such as whey permeate, starch hydrolysates which are sources of lactose and glucose respectively.

Lately, the potential of lactic acid as a starting feed stock for a new class of renewable biodegradable lactide polymers has been recognized. These biodegradable polymers are considered as a replacement for present plastic materials or for various new uses such as in development of support and attachment membrane used in bone surgery, service plastic ware and containers, medical garments, disposable diapers, yard waste bags etc., in which biodegradability is preferred.

For the different applications, varying purity of grades or lactic acid is used. For technical purposes like in metal and leather, low technical grade lactic acid is used; slightly more purified food grade Lactic acid is used in food related applications. High purity grade is used in pharmaceutical applications. Whereas, in case of use of lactic acid as starting feed stock for lactide polymers, exceptionally pure, thermally stable grade, especially the free isomeric L- or D-form is preferred.

India has abundant renewal agricultural resources that can be utilized as feed stocks for the production of lactic acid, which is a building block for the manufacture of polylactic acid (PLA).

Polylactic acid (PLA) is a biodegradable polymer derived from lactic acid. It is a highly versatile material and is made from 100% renewable resources like corn, sugar beet, wheat and other starch-rich products. Polylactic acid exhibits many properties that are equivalent to or better than many petroleum-based plastics, which makes it suitable for a variety of applications. Polylactic acid is a versatile polymer that has many potential uses, including many applications in the textile and medical industries as well as the packaging industry. Polylactic acid also has many potential uses in fibers and non-wovens. It is easily converted into a variety of fiber forms using conventional melt-spinning processes.

It is estimated that known global resources of oil will run dry in 80 years, natural gas in 70 years and coal in 700 years, but the economic impact of the depletion could hit much sooner; since prices will soar as resources are depleted. It is clear that researchers need to work toward replacing fossil fuel resources with renewable resources for many petroleum-based products. Headway is being made with a polymer called polylactic acid (PLA), an affordable, recyclable, innovative material made from renewable resources. Production of polylactic acid from renewable agricultural feed-stocks is an attempt to balance the resources and create plant based replacement for fossil-fuels. In addition, the excellent biodegradability of lactic acid based polymers and their environmental friendly nature of recyclability/compostability have further increased their potential and need for development.

The present invention is an attempt in this direction by providing an efficient process for producing polylactic acid from renewable agricultural feedstock like starchy materials, cellulosic materials like wood, cane bagasse, wheat straw, rice straw molasses, derived from cane or beet root.

Lactic acid can be manufactured by either chemical synthesis or renewable carbohydrate fermentation commercially. With increased public concern and government regulations on greenhouse gas emissions and environmental pollution, lactic acid produced by environmentally compatible fermentation bioprocesses, using renewable biomass resources, is preferable to chemical synthesis using fossil-fuels (coal, petroleum, or natural gas).

Polylactic acid is not a new material. It has been around for decades. In 1932, Wallace Carothers, a scientist from Dupont, produced a low molecular weight product by heating lactic acid under a vacuum. In 1954, after further refinements, Dupont patented Carothers' process.

Due to high costs, the focus since then has been mainly on the manufacture of medical grade sutures, implants and controlled drug release applications. The cost of production of the monomer has been a deterrent to widespread development of the polymer. Recently, there have been advances in fermentation of glucose, which turns the glucose into lactic acid. This has dramatically lowered the cost of producing lactic acid and significantly increased interest in the polymer.

Lactic acid, 2-hydroxy propionic acid or a-hydroxy propionic acid is manufactured/produced by synthetic and fermentation methods for use in food preservation, pharmaceuticals, leather tanning, and metal pickling as a starting material in specialized chemical processes. Two optically active isomeric (enantiomeric) forms of lactic acid are designated L(+) or S(+)-dextrorotary and D(−) or R(−) levorotary as shown below,

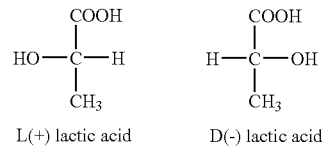

Chemical synthesis of lactic acid results in a racemic mixture wherein both enantiomers are present in equal proportion, whereas microbiological process produces predominantly one of the enantiomer.

L-lactic acid is necessary to produce biodegradable polymer. Production of L-lactic acid is normally achieved by selecting suitable microbial strain in the process of fermentation. It involves conversion of monosaccharides such as glucose, fructose, galactose or disaccharides such as sucrose or lactose into lactic acid. A few homofermentative strains producing only lactic acid as a product include *Lactobacillus delbruekii, L. casei, L. acidophilus, L.bulgaricus*. The former consumes sucrose, glucose or fructose but no lactose while the latter three species consume lactose and galactose in addition to the other sugars. The biological production of lactic acid is complicated due to inhibition caused by drop in pH due to lactic acid production and expensive downstream processing to produce lactic acid from dilute aqueous fermented broths. The conventional method of lactic acid production is the anaerobic fermentation by *Lactobacillus* sp. in batch reactors. In order to keep the fermentation process continuous, the acid produced is neutralized with alkali or removed from the fermentation system. The conventional processes employs calcium carbonate or sodium hydroxide to neutralize the acid produced. The corresponding lactate is then separated from the broth by various processes involving solvent extraction, electro-dialysis, or distillation or a combination of one or more process.

Production of polylactic acid requires high purity lactide obtained from predominantly L-lactic acid generated biochemically from edible renewable resource like carbohydrate feed-stocks. The conventional industrial processes involve removal of biomass from fermentation broth followed by acidification, purification, concentration and polymerization. The present invention describes an efficient process wherein L-lactic acid is predominantly produced from the fermentation of a cheap renewable agricultural feed-stock like molasses or cane bagasse hydrolysate which is separated, purified and concentrated concurrently to produce crude lactide which is polymerized to polylactic acid after further purification.

Fermentative production of lactic acid is the commonly used method for obtaining optically pure isomer required for production of polylactic acid. U.S. Pat. No. 6,475,759 (Nov. 5, 2002) granted to Carlson et al., provides a low pH lactic acid fermentation, which includes incubating acid tolerant homolactic bacteria in nutrient medium to produce a fermentation broth with high levels of free lactic acid. It also provides isolated acid-tolerant homolactic bacteria capable of producing high levels of free lactic acid. This patent relates specifically to bacteria capable of tolerating low pH and hence would be confined to the process, which would utilize that particular bacterial strain. The fermentation process employed herein is of batch type. Further the prior art uses calcium carbonate to neutralize the acid produced, which ultimately generates large amount of calcium sulfate (gypsum), which can pose a waste disposal issue, and calcium sulfate is considered to be an undesirable environmental concern.

Corn syrup, starch, corn-steep liquor, corn oil, milk-whey, sugar, beet and sugarcane juice are commonly used as feedstock for the process of fermentation. EP Pat No 0393818 A1 (Glessner, David A. et al;) provides a process for producing and purifying lactic acid, which comprises of growing a lactic acid producing microorganism on an inexpensive substrate containing carbohydrate, corn steep liquor and corn oil until most of the carbohydrate is converted to lactic acid. All these materials are of high value as food. In fact the cost of substrate is one of the current problems in the cost effective production of lactic acid by fermentation. The inventors of the present invention have used a cheap substrate, byproduct/waste product of sugar industry, molasses and cane bagasse hydrolysate as feed stock for lactic acid fermentation which does not have any value as food.

The above mentioned patent relates to a process for producing and purifying lactic acid by fermentation using robust strain of a lactate producing microorganism which produces lactate salt in high concentration from a low cost fermentation medium and a purification process which uses conventional electrodialysis to recover and concentrate the lactate from a whole broth containing cells and nitrogenous impurities; a water-splitting electrodialysis to convert the lactate obtained to lactic acid and base treatment with ion exchangers to remove charged impurities from the lactic acid. This process has limitations since expensive electrical energy, rather than other energy sources, is used to drive the process forward. Furthermore, polymeric membranes used in the process of electrodialysis are very sensitive to impurities and applying them to fermentation products of molasses would require costly purification operation.

EP Pat No 0790229A1 (Donald McOulgg, et al;) describes a process for the recovery of lactic acid from a medium by contacting it with a solid-phase free base polymer having tertiary amine or pyridine groups to absorb lactic acid. The lactic acid is later desorbed using a stronger acid or hot water. Loading of the resins by other undesirable ionic and acidic species in the fermentation broth, requirement of high regeneration efficiency and fouling of these resins by large organic molecules, pigments present in the broth are the major limitations of the process.

U.S. Pat No 6,569,989 (Ohara et al.), U.S. Pat. No. 6,326,458 (Gruber, et al.) and WO 93/00440 (Michael Cockrem et al;) relate to processes for producing lactide and polylactic acid from lactic acid obtained by fermentation, synthesizing lactate ester from lactic acid, distillation of lactate ester, polycondensation of the lactate ester in the presence of a catalyst to get a prepolymer of molecular weight in the range of 5000-15000, depolymerisation of prepolymer to get lactide and its ring opening polymerization whereby polylactic acid is obtained. Hydrolysis of the ester results in the lactic acid, if desired. This process involves the two steps of energy intensive distillation and in addition has the possibility of racemization.

U.S. Pat. No. 6,472,559 (Avraham et al;), EP Pat No 0804607 B1 (Abraham. M. Baniel, et al;) and U.S. Pat. No. 6,087,532 (Abraham. M. Baniel) describes a process, for the separation and recovery of lactic acid from fermentation broth using mixed solvents in the presence of $CO_2$ and back extraction with water at elevated temperature of 80-240° C. The process generally involves preconcentration of the feed solution by water removal to the level of 40-70%, which is energy intensive. The process is associated with the limitations such as use of expensive solvents like high molecular weight trialkyl amines, difficulties in handling mixtures of solvents, their recovery and other associated problems.

U.S. Patent No. 5,369,122 (Steinmetzer) discloses a method for producing a humectant containing neutralized, concentrated L-2-pyrrolidone-5-carboxylic acid and lactic acid from sugar-free or partially desugarized residual molasses from sugar beet molasses. It involves preparation of sugar-free or partially desugarized residual molasses from sugar beet molasses by chromatographic separation of sugar beet molasses, using ion exclusion into fractions and separating the acids through steps of extraction and ion-exchange, and/or cation exchange and anion exchange, and/or cation exchange and elution with alkali metal hydroxide. The need for chromatographic separation of sugar beet molasses to obtain sugar-free or partially desugarized residual molasses for the recovery of acids, however, makes the process less attractive.

U.S. Pat. No. 5,310,865 (Katashi Enomoto et al;) discloses a process for making polyhydroxy carboxylic acid by conducting a dehydration condensation of a hydroxycarboxylic or an oligomer in a reaction mixture containing an organic solvent. The organic solvent is used to remove the water of condensation by azeotropic distillation. Preparation of very high molecular weight polymer above 1,00,000 required for many applications is one of the limitations of the process on account of difficulties associated with the removal of trace amounts of moisture.

The continuous process disclosed in U.S. Pat. No. 6,326,458 (Patrick Richard Gruber et al;) for the manufacture of lactide and lactide polymers involves preparation of lactide and lactide polymer from lactic acid or an ester of lactic acid in the presence of catalyst giving crude polylactic acid, prepolymer and a reaction by-product in the case of ester. The crude lactide obtained from prepolymer is purified by distillation again before being used for polymerization. The generation of by product in the case of lactic acid ester as starting material and the energy intensive step of distillation of crude lactide are constraints adding substantially to the cost of the process.

All the prior art methods for the production of lactic acid by fermentation either require relatively pure substrates for the growth of the bacteria and/or complex and toxic solvents for separation of lactic acid. Also, there are difficulties in recovering the solvents and high energy is utilized for separating such solvents by distillation. Thus, these processes are costly and time consuming. Some of the prior art provides a low pH lactic acid fermentation which includes incubating acid tolerant homolactic bacteria in nutrient medium to produce a fermentation broth with high levels of free lactic acid. Further the prior art uses calcium carbonate to neutralize the acid produced which ultimately generates large amount of calcium sulfate (gypsum), which can pose a waste disposal issue as calcium sulfate is considered to be an undesirable environmental concern.

Looking to the dire need of the hour, the scientists of the present have developed a novel process of producing polylactic acid, from fermentation of non-edible renewable agricultural feed stocks.

According to the present invention, polylactic acid is produced from fermentation of non-edible renewable agricultural feed stocks, the present process is found to be relatively cheaper as compared to conventional processes wherein starchy substrates are being used as a raw material.

In the present process, the pH adjustment is accompanied by using Ammonia, which does not form the salt precipitate (Gypsum) as in the conventional process. The present process is devoid of the formation of salt precipitate, thus the problem associated with the waste disposal issue has been resolved by the present invention.

Compared to the conventional process, the present invention provides a process wherein a single bulk solvent is used for the separation of lactic acid from fermentation broth at ambient temperature in comparison to a mixture of expensive solvents and pre concentration steps used in some of the conventional processes.

Further, the present invention provides a process wherein the regeneration/recovery of the solvent in the process are almost quantitative without any energy step of high temperature operation and/or distillation. The solvent thus regenerated is recycled for extraction without any further treatment.

In the present process the step of prepolymerization and lactide formation is combined in a single unit operation. Also the invention provides a process wherein the separation, concentration and purification is achieved concurrently using affinity driven processes at ambient temperature instead of energy driven processes employed in some of the conventional processes.

The present process developed by the inventors is efficient, cost effective and less cumbersome as compared to the conventional process.

It is still an object of the present invention to provide a process for producing polylactic acid from renewable feed stocks such as molasses as such without need for chromatographic separation by ion exclusion for better economics of the process.

OBJECTS OF THE INVENTION

It is an object of the present invention to provide an efficient process for producing polylactic acid, from renewable agricultural feed-stocks as starting material. The extraction efficiency of the process of the subject invention is over 90% as against 90% as claimed by the conventional processes.

It is an object of the present invention to provide an efficient process for producing polylactic acid from renewable agricultural feed stocks such as molasses and cane bagasse hydrolysates which otherwise is a waste product of sugar industries, in the most efficient way to manufacture PLA and hence very cost effective.

It is still an object of the present invention to provide a process that can be successfully applied to other renewable agricultural feed stocks such as corn syrup, sugar-beet, cane juice.

It is still an object of the present invention to provide a process using a single bulk solvent for the separation of lactic acid from fermentation broth at ambient temperature in comparison to a mixture of expensive solvents and pre concentration of fermented broth used in some of the other processes.

It is still an object of the present invention to provide a process wherein the regeneration/recovery of the solvent in the process of the present invention is almost quantitative without any energy step of high temperature operation and/or distillation.

It is still an object of the present invention to provide a process wherein the step of back-extraction utilizes the hydroxides of alkali or alkaline earth metals, is affinity driven and less energy intensive as against temperature driven and energy intensive operation of some of the other processes. The solvent thus regenerated is recycled for extraction without any further treatment.

It is still an object of the present invention to provide a process wherein the concentrated lactic acid solution is used directly for the formation of lactide in a reactor at high vapour temperature between 120° C. and 155° C with a corresponding liquid temperature of 180° C.-225° C. under a vacuum of 5-30 mm of Hg combining the step of prepolymerization and lactide formation into a single unit operation.

It is still an object of the present invention to provide a process wherein the purification of lactide is done by crystallization with organic solvents wherein the mother liquor is recycled for further preparation of lactide. Purification by vacuum distillation involving very high vacuum and energy is disclosed in some of the other processes.

To these ends, the present invention is concerned with a process for producing polylactic acid from fermentation of renewable agricultural feed stocks comprising molasses or cane bagasse employed as a starting material containing sugars with all other substances present in molasses and cane bagasse, together with a nitrogen source selected from corn steep liquor, and autoclaved yeast paste, the process comprising the steps of;

i) preparing a fermentation medium having molasses as a carbon source;

ii) fermenting the fermentation medium;

iii) extracting lactic acid from the fermentation medium using organic solvent and back extracting into the aqueous phase using hydroxide of ammonia, alkali or alkaline earth metal;

iv) purifying the lactic acid solely with cation exchange resin, and concentrating the purified lactic acid;

v) preparing lactide from the lactic acid;

vi) polymerizing the lactide to form the polylactic acid;

vii) the renewable agricultural feed stock is cane molasses containing about 40% to about 50% (w/w) fermentable sugars; and viii) the renewable agricultural feed stock comprises cane bagasse, and preparing the cane bagasse by hydrolyzing the bagasse particles with dilute acid for 30 -90 min at 120° C. and treating the bagasse with 1-5% (w/v) alkali at 120° C. to 150° C. for a period of about 15 to about 90 minutes for delignification.

In the process of the invention, the renewable agricultural feedstocks may be edible or non-edible.

In the process, the renewable agricultural feed stock is cane molasses containing about 40% to about 50% (w/w) fermentable sugars.

In the process of the invention, the molasses is adjusted to a fermentable sugar concentration of about 70g/L.

In the process of the invention, the molasses is centrifuged to remove suspended materials and diluted with water to produce a fermentable sugar concentration of about 7% to about 10%.

The process further comprises a step of supplementing the molasses solution with about 2% to about 5% of the corn steep liquor and the autoclaved yeast paste.

In the process of the invention, the fermenting step is carried out under anaerobic/microaerophilic conditions.

In the process of the invention, the fermentation under anaerobic/microaerophilic conditions are carried out by microbe selected from the group consisting of *Lactobacillus, Streptococcus, Bacillus* and *Rhizopus*.

In the process of the invention, the lactobacillus is selected from the group consisting of *L. delbrueckii, L. rhamnosus, L. helveticus, L. casei, L. plantarum, L. bulgaricus, L. amylovorans* and *L. lactis*.

In the process of the invention, the fermenting step further comprises a step for adjusting and maintaining the pH of fermentation medium to between about 5.0 and about 6.0, thereby avoiding growth retardation of the microbe.

In the process of the invention, the fermenting step is a continuous process or a fed batch fermentation process.

In the process of the invention, the step of adjusting the pH of the fermentation medium is accomplished by employing a neutralizing agent selected from the group consisting of alkali, carbonates and ammonia.

In the process of the invention, lactic acid produced in the fermentation medium is extracted using organic solvents.

In the process of the invention, the extracting step employs organic solvents selected from the group consisting of isoamyl alcohol, butanol, cyclohexanone and methyl acetate.

In the process of the invention, the extracting step further comprises employing a solvent for separating the lactic acid from a fermentation medium at ambient temperature.

In the process of the invention, the solvent is an alcohol or an ester.

In the process of the invention, the process has an extraction efficiency of over 90%.

In the process of the invention, the extracting step is not energy intensive.

In the process of the invention, the extracted lactic acid is back extracted into aqueous phase, purified and concentrated.

In the process of the invention, the step of back extraction of the lactic acid into aqueous phase from organic solvent is achieved using hydroxide of alkali or hydroxide of alkaline earth metals.

In the process of the invention, the back extracted lactic acid in the aqueous phase is acidified using concentrated sulphuric acid to a pH ranging between 2- 2.5.

In the process of the invention, the purification involves passing the back extracted lactic acid through a cation exchange resin without elution by alkali.

In the process of the invention, the purified lactic acid is concentrated in a packed glass lined distillation column.

In the process of the invention, the concentrated lactic acid is converted into lactide in a reactor at a vapour temperature between about 120° C. and about 155° C. with a corresponding liquid temperature of about 180° C. to about 225° C.

In the process of the invention, the conversion of lactic acid to lactide is carried out under a vacuum of about 5 to about 30 mm of Hg and combines prepolymerization and lactide formation into a single operation.

In the process of the invention, the purification of lactide comprises a step of crystallization using organic solvents.

In the process of the invention, the purified lactide is polymerized to give polylactic acid.

In the process of the invention, an important feature is that the renewable agricultural feed stocks are selected from the group consisting of molasses, cane bagasse hydrolysates, corn syrup, sugar-beet, and cane juice.

Another important feature of the invention is that it is directed to a process for producing polylactic acid from fermentation of renewable agricultural feed stocks comprising molasses or cane bagasse employed as a starting material containing sugars with all other substances present in molasses and cane bagasse, together with a nitrogen source and other microbial growth constituents selected from corn steep liquor, and autoclaved yeast paste, the process comprising the steps of; i) preparing a fermentation medium having molasses as a carbon source; ii) fermenting said fermentation medium; iii) extracting lactic acid from said fermentation medium using organic solvent and back extracting into the aqueous phase using hydroxide of ammonia, alkali or alkaline earth metal; iv) purifying said lactic acid with cation exchange resin without elution with alkali metal hydroxides, avoiding the use of any anion-exchanger, and concentrating said purified lactic acid.

In the process of the invention, an important feature is that the renewable agricultural feed stock comprises cane bagasse hydrolysate, and the cane bagasse hydrolysate being prepared by hydrolyzing cane bagasse particles with dilute acid for 30 -90 min at 120° C. and treating the bagasse with 1-5 % (w/v) alkali at 120° C. to 150° C. for a period of about 15 to about 90 minutes for delignification.

It is still an object of the present invention to provide a process wherein the separation, concentration and purification is achieved concurrently using affinity driven processes at ambient temperature instead of temperature or electricity driven processes employed in some of the other processes.

The foregoing and still other objects and advantages of the present invention will be more apparent from the following detailed explanation of the preferred embodiments in connection with the accompanying drawing.

DETAILED DESCRIPTION OF THE INVENTION

Figure 1:
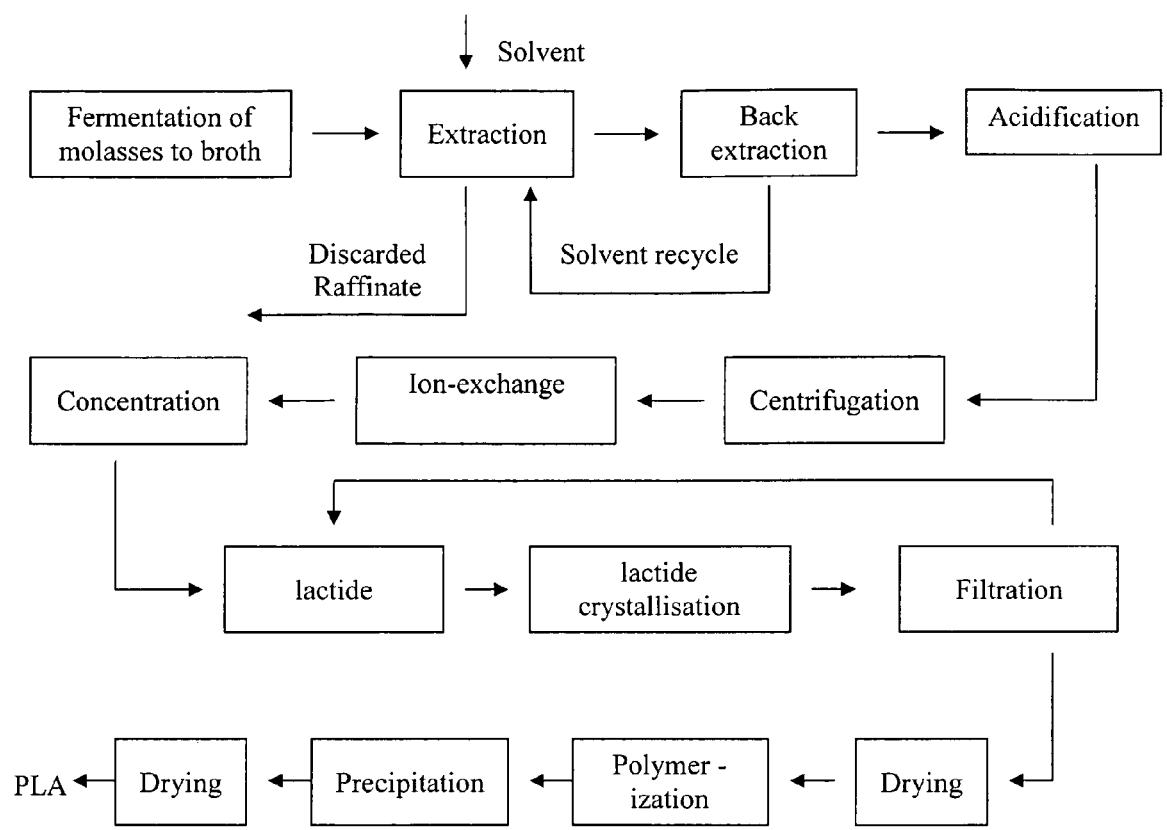
FIG. 1 is a block diagram depicting the production of polylactic acid from fermentation of molasses according to one embodiment of the present invention.

The present invention describes a process for the production of polylactic acid, using renewable agricultural feed stocks such as molasses and cane bagasse hydrolysates raw material. The renewable agricultural feed stocks employed may be either edible or non-edible. The process according to the present invention comprises the fermentation of raw material to lactic acid and its separation from fermented broth and its conversion to lactide and polylactic acid. The process according to the present invention comprises the steps of:
  i. Preparation of lactic acid medium using either cane molasses or cane bagasse as raw material;
  ii. Fermentation of lactic acid;
  iii. Separation of lactic acid; and
  iv. Preparation of lactide and PLA.

In one aspect of the present invention, fermentation medium was prepared using either cane molasses or cane bagasse as a raw material.

In the present invention, the fermentation medium was prepared using cane molasses containing about 40-50% (w/w) fermentable sugars was centrifuged to remove suspended materials and diluted with water to get a final fermentable sugar concentration of 7-10% (w/w). The medium was supplemented with other nitrogen source and other growth constituents. In large scale processing the diluted molasses solution is enriched with 2-5% corn steep liquor and autoclaved yeast paste.

The fermentation medium using cane bagasse as a raw material was prepared by hydrolyzing bagasse particles with dilute acid for 30-90 min at 120° C. The hydrolyzed bagasse was further treated with 1-5% (v/v) alkali at 120° C. to 150° C. for a period of 15-90 min for delignification. The cellulose portion thus obtained was subjected to enzymatic hydrolysis with cellulase enzyme.

The cane bagasse hydrolysate which is rich in glucose was supplemented with nitrogen source prior to fermentation.

In accordance with the present invention, the fermentation of lactic acid was carried out under anaerobic/microaerophilic conditions by employing strains of the bacterial genus like *Lactobacillus* in batch mode for 24-48 hours. In a preferred embodiment in accordance with the present invention, the *Lactobacillus* strain employed is *L. delbrueckii*.

In accordance with the present invention, the pH of the fermentation medium was readily obtained by way of pH adjustment employing neutralizing agent. The neutralizing agent that may be used in accordance with the present invention to maintain the suitable pH level is selected from either alkali or carbonates or ammonia solution. The pH of the medium during fermentation was constantly maintained between 5.0 to 6.0 using alkali or carbonates or ammonia solution. The temperature of the fermentation was maintained between 37° to 45° C. After fermentation was completed the broth containing lactic acid was clarified by centrifugation for further downstream processing.

The clarified fermented broth was extracted using organic solvents such as isoamyl alcohol, butanol, cyclohexanone, methyl acetate, etc. at ratios ranging from 1:1 to 1:5 employing suitable contact equipment such as rotary disc contactor. The extract was taken for further processing. The extraction efficiency obtainable was over 90% by the present invention. The lactic acid containing extract was contacted with aqueous alkali like ammonia, lime, caustic etc in the ratio of 1:3 to 1:10. The mixture was stirred for 1 hour and allowed to settle for 2 hours for phase separation to occur. The aqueous phase containing lactic acid salt was separated from organic extractant and taken for its down stream processing. The organic layer was recycled for extraction. The aqueous phase containing the lactic acid salt was treated with mineral acid for the separation of lactic acid and the salt formed, if any, was collected by centrifugation. The crude lactic acid thus obtained was treated with cationic resin to remove any traces of metal ions and concentrated at least 5-6 fold by vacuum distillation.

In another aspect of the present invention, the concentrated lactic acid was converted into lactide in a jacketed stirred tank reactor provided with vacuum and heating facility. Initially the contents were heated to 120-150° C. to remove water and subsequently catalyst in the range of 0.05 to 2.0% (w/w) was added. The reaction was continued for another 5-24 hours wherein temperature was increased progressively from 140 to 275° C. and vacuum was increased progressively up to 1-20 mm of Hg. After the removal of residual water, the lactide formed was distilled out and collected in chilled receiver.

The lactide obtained was further purified by crystallization with organic solvent such as ethyl acetate, toluene or alcohol. The purified lactide was polymerized in the presence of suitable catalyst in a stirred tank reactor. The temperature was maintained between 120°-200° C. for a period of 1-20 hours. The resultant polymer, polylactic acid (PLA) was dissolved in a suitable solvent and precipitated in another solvent used as a coagulant for its characterization. The resultant product was dried and characterized.

The inventors of the present invention have developed a novel process that differs from those disclosed earlier or the known art for the production of PLA in the sense that the present process effectively makes use of cheap waste product of sugar industry for the fermentation of lactic acid and its recovery from the fermentation broth. The present invention further provides for the concentration and purification of lactic acid for further down stream processing for the preparation of lactide and PLA. The approximate concentration of lactic acid in the fermentation broth is in the range of about 4.5% to about 5.0% w/v which is extracted with a suitable organic solvent such as alcohols, ketone, esters and ethers in LLE equipments such as mixer—settler, packed column, rotating disc contactor, or pulsed extraction column with sufficient residence time ranging from half an hour to 1 hour and volume ratios of 1:1, 1:1.25, 1:1.5, 1:2, 1:3, 1:4 and so on to get extraction efficiencies above 90% resulting in good phase separation between the raffinate (aqueous layer) and the extract (organic layer) phases.

The solvent extract phase containing the lactic acid and some impurities which add color to the extract phase is then treated with a known quantity of alkali or alkaline earth metal hydroxides such as sodium hydroxide, calcium hydroxide, ammonium hydroxide and the like in an conventional agitator vessel with proper agitation for half an hour to 1 hour and then allowed to settle down for an additional time for good phase separation. The aqueous layer containing lactic acid is drained off for down stream processing. The extract (organic layer), the regenerated solvent is removed and then recycled back to the LLE equipment for reuse as mentioned above.

The aqueous phase containing the salt of the lactic acid, referred as lactate, is then treated with a mineral acid like sulphuric acid to precipitate the metal salt at a pH less than the pH value of the lactic acid viz 3.86 more preferably at pH of less then 3 and most preferably at a pH between 2.5 and 3.0. The acidified lactate solution is then centrifuged to get rid off the metal salt in the form of a cake which is then washed thoroughly with demineralized water to extract the adsorbed lactic acid, if any which is then recycled to the metal precipitation step. The filtered aqueous centrifuged/filtered liquid is then taken for further down stream, processing.

The residual metal ion in the dilute lactic acid of concentration ranging between 9% and 10% w/v, is then removed in a continuous column packed with an ion-exchange resin with suitable flow rate adjustments of the entering and exit streams. The end point of the column treatment operation is indicated by the value of pH or direct measurement of the metal ions.

The dilute lactic acid solution is then concentrated in a packed distillation column to a level of 50-60% w/v with proper reflux ratios in the range between 1:3::1:5 under a vacuum of around 300-350 mm and a temperature between 75° C. and 85° C. The distillate collected, which is mainly water, is then recycled to the precipitation step. The concentrate at the bottom of the boiler of the distillation column is then sent for the production of lactide.

The concentrated lactic acid is then taken in stirred tank reactor of suitable capacity with proper material of construction, agitation and heating/cooling facilities in a jacket as well as down stream condensers of suitable surface area. The lactide of required specification is obtained at a vapour temperature of 120-155° C. and liquid temperature between 190-225° C. under a vacuum of 10 mm-30 mm of Hg with suitable catalyst and removal of free and bound water during the course of reaction. The residue of the autoclave contains unconverted lactic acid, trimers and other high-boiling components. The average yield of lactide varies between 75% and 80% of the theoretical quantity.

The crude lactide obtained as above is further purified by crystallization using organic solvents like ethyl acetate, ethanol, methanol, butanol and a host of other solvents. The crystallized lactide is then filtered off. The purified lactide is further recrystallised with some solvents so as to remove the colored substances completely. The yield of purified lactide is in the range of 50-60%. The mother liquor can be further reprocessed/recycled to produce lactide.

The purified and crystalline lactide is then polymerized in the presence of a suitable catalyst based on calcium, zinc or tin compounds in a stirred tank reactor with heating/cooling coils under proper agitation and temperature profile varying between 185° C. and 110° C. for around 15-20 hours. The resultant polymer product (PLA) is then dissolved in a suitable solvent, precipitated in another solvent acting as a coagulant, and dried. Polymer of molecular weight ranges between 20,000 and 1,00,000 is obtained which can be used for various applications.

In accordance with the present invention the fermentation can be carried out using the microbial cells of suitable strain for the production of various metabolites. In some of the embodiments in accordance with the present invention for the production of lactic acid, the microbial cells that may be employed is selected from strains of the bacterial genus like *Lactobacillus, Streptococcus, Bacillus* or molds like *Rhizopus*. The different strains of *Lactobacillus* used in accordance with the present invention for lactic acid production can be selected from *L. delbrueckii, L. rhanmosus, L. helveticus, L. casei, L. plantarum, L. bulgaricus, L. amylovorans, L. lactis*, or the like. In a preferred embodiment in accordance with the present invention, the Lactobacillus strain employed is *L. delbrueckii*.

In accordance with the present invention fermentation can be either a continuous fermentation process, a batch fermentation process or a fed batch fermentation process. Preferably the process of the present invention comprises culturing the bacterium in a batch fermentation process.

The process flow sheet described above for the production of PLA or a salt thereof from molasses is depicted in FIG. 1.

The present invention relating to a multi-steps process chain for the manufacture of PLA from fermentation of molasses has advantages over others in terms of the following:

1. This process utilizes the renewable agricultural feed stock of molasses, which otherwise is a waste product of sugar industries in the most efficient way to manufacture PLA and hence very cost effective. This process can be successfully applied to other renewable agricultural feed stocks such as corn syrup, sugar-beet, cane juice which are relatively cleaner with respect to molasses in terms of contamination.

2. The process as mentioned above uses a single bulk solvent for the separation of lactic acid from fermentation broth at ambient temperature in comparison to a mixture of expensive solvents and pre concentration steps used in some of the other processes. The extraction efficiency in this process was above 90% as against 90% claimed by others.

3. The regeneration/recovery of the solvent in the subsequent step in this process are almost quantitative without any energy step of high temperature operation and/or distillation.

4. The step of back-extraction utilizes the hydroxides of alkali or alkaline earth metals is affinity driven and less energy intensive as against temperature driven and energy intensive operation of some of the other processes. The solvent thus regenerated is recycled for extraction without any further treatment.

5. The concentrated lactic acid solution is used directly for the formation of lactide in an autoclave at high vapour temperature between 120° C. and 155° C. with a corresponding liquid temperature of 180° C.-225° C. under a vacuum of 5-30 mm of Hg combining the step of prepolymerization and lactide formation in a single unit operation.

6. Purification of lactide is done by crystallization with organic solvents wherein the mother liquor is recycled for further preparation of lactide. Purification by vacuum distillation involving very high vacuum and energy is disclosed in some of the other processes.

7. Separation, concentration and purification is achieved concurrently using affinity driven processes at ambient temperature instead of temperature or electricity driven processes employed in some of the other processes.

The present invention will now be illustrated by means of some examples. These examples show how the present invention has been practiced, but should not be construed as limiting. Most of the experimental work was done using laboratory set-up/equipment. Various stages of the process were carried out using laboratory scale, bench scale or pilot scale equipments, continuously or batch wise as a single process step/unit operation to demonstrate the feasibility of using such process technology on a commercial scale.

EXAMPLE 1

To 250 ml of fermentation medium containing cane molasses adjusted to a final fermentable sugar concentration of 70 g/L and enriched with corn steep liquor (25 g/L) and yeast extract (10 g/L), 24 h old culture of *Lactobacillus delbreuckii* was added as inoculum at 10% final concentration. The fermentation was carried out in shake flasks at 42° C. for 72 h at 150 rpm in a Gallenkamp incubator shaker. The pH of the fermentation broth was maintained at 6.0 using $CaCO_3$. The yield of lactic acid at the end of 72 h was 50 g/L.

EXAMPLE 2

A 2 L batch of the fermentation medium containing cane molasses and supplemented with 25 g/L corn steep liquor and 10 g/L yeast extract, was run in a 2.5 L bioreactor. The initial sugar concentration was adjusted to 70 g/L. The medium was inoculated with 200 ml of 24 h old culture of *Lactobacillus delbreuckii*. The fermentation was carried out at 42° C. for 48 h at 200 rpm agitation. The pH of the medium as maintained at 6.0 using liquid ammonia. The lactic acid yield was 66 g/L at the end of the run.

EXAMPLE 3

The lactic acid fermentation was scaled up in a 500 L fermentor with a working volume of 350 L. The medium containing cane molasses (adjusted to 70 g/L sugar), corn steep liquor (25 g/L) and yeast extract (10 g/L) was inoculated with 24 h old culture of *L. delbrueckii* (35 L) grown in a 100 L fermentor. The fermentation was carried out at 42° C. for 48 h at 200 rpm agitation with pH maintenance at 6.0 with liquid ammonia. The yield of lactic acid was 50 g/L.

EXAMPLE 4

The lactic acid fermentation was also set up in a 1000 L fermentor. The batch size was 800 L. The medium composition is same as Example 1. *L. delbreuckii* inoculum (80 L) for this batch was raised in a 100 L fermentor. The fermentation was done at 42° C. for 48 h at 200 rpm agitation. The pH of the medium as maintained at 6.0 using liquid ammonia. The lactic acid yield was 55 g/L at the end of 48 h of fermentation.

EXAMPLE 5

40 ml of a fermentation broth, obtained by fermentation of sugars present in molasses by *Lactobacillus delbruckii*, after centrifugation and lowering of pH to 2.0, containing 5.8% (w/v) of lactic acid determined colorimetrically, 4% total sugar and total dissolved solids of 20% was solvent extracted with iso-amyl alcohol in the volume ratio of 1:2 under agitation on a rotary shaker for 30 mins. The fermentation broth contained various metal ions in different concentrations. The concentration of the metal ions measured by ICP is as follows: titanium, 1.76; chromium, 37.53; manganese, 578.30; iron, 2117.3; cobalt, 42.22; nickel, 7.62; copper, 7.038; zinc, 123.75; aluminum, 52.20; lead, 13.49; molybdenum, 1.76; arsenic, 1.17; sodium, 105.4; potassium, 129.03; magnesium, 35.07; calcium, 11.55 (all the values are expressed as parts per million). The phases were allowed to separate in a 250 ml separating funnel for 1 hr. The aqueous phase was re-extracted with a fresh portion of the alcohol in the same volume ratio after taking into consideration volume changes due to mutual dissolution of the two liquid phases. After 5 such liquid-liquid extractions, the raffinate was centrifuged at 7000 rpm for 15 mins to remove entrained organic phase and analyzed for lactic acid. From mass balance, the recovery of lactic acid in the solvent was estimated to be 94% with over 90% removal of sugar.

EXAMPLE 6

10 ml of fermentation broth similar to that described in example 1 at a pH of 2 was mixed with 100 ml of di-isopropyl ether (DIE) in a 250 ml conical flask and kept on a rotary shaker for 1 hr. During the process of extraction, formation of emulsion was observed which on centrifugation at 7000 rpm resulted into phase separation. Subsequent four-stage repeated extraction of aqueous phase with DIE resulted in combined organic phase practically colorless indicating almost complete removal of color (>99%) with decrease in lactic acid concentration in the aqueous phase from 5.8% to 1.8%.

EXAMPLE 7

50 ml of fermentation broth with augmented concentration of lactic acid (7.7 wt %) of pH 2 was subjected to liquid/liquid extraction with 100 ml of cyclohexanone in separating funnel of capacity 250 ml. The mixture was mixed thoroughly for an hour and allowed to settle. After separation of the two phases, the bottom aqueous layer was subjected to two more liquid/liquid extractions. After the three-stage extraction, the raffinate had 0.8 wt % of lactic acid indicating a recovery of 90%. Extraction was advantageous both in terms of sugar and color removal from the fermentation broth. After the first extraction the organic layer was found to have sugar-to-lactic acid ratio of nil and color-to-lactic acid ratio of 0.65 in comparison to 0.23 and 5.6 respectively for the fermentation broth.

EXAMPLE 8

1-Butyl alcohol was tested for extraction efficiency in respect of lactic acid, using the fermentation broth employed in Example 1. Broth-to-extractant ratio employed was 1:0.73 by weight. The mixture was put on a rotary shaker for 1 hr, and allowed to settle under quiescent conditions for another 1 hr for phase separation to occur. The extract phase thus obtained was further extracted with 1N NaOH (1:2 volume ratio, 1 hr mixing on a rotary shaker), whereupon the alkaline phase was found to contain 16.2 g/L of sodium lactate.

EXAMPLE 9

In an experiment, an extractant comprising of 150 ml of the ethyl ester of ethanoic acid was contacted with 46% of its weight of the fermentation broth that was employed in Example 3 in a 500 ml stoppered glass bottle using rotary shaker for 1 hr., and then the contents were transferred to a 500 ml separating funnel and left undisturbed for phase separation to occur. The raffinate was contacted again with fresh extractant in the same volume ratio. After three serial extractions, the spent aqueous phase showed a reduction in lactic acid concentration, the final level being only 21% of the initial value. While the color of the broth was dark brown, combined extracts had very little color. After factoring out dilution effects, about 98% of color was found to be retained by the raffinate.

EXAMPLE 10

Effect of pH on the efficiency of extraction by 1-octanol was investigated, using a fermentation broth with a lactic acid content of 72 g/L. In one case, the broth with a pH of 6.2 was used as such, while the pH of a second broth sample was adjusted to 3.5, and that of a third one to 3.0. In all the cases, 5 ml broth was contacted with 10 ml alcohol, mixed manually for 30 min., and phases separated after an appropriate period of settling. By measurement of lactic acid in raffinate, it was ascertained that recovery of lactic acid corresponding to pre-extraction pH of 6.2, 3.5 and 3.0 was <1%, 22% and 44% respectively. Thus, lower pH values enhance extraction efficiency to a considerable extent.

EXAMPLE 11

Fermentation broth containing 56 g/L lactic acid of pH 2 was extracted, an appropriate number of times with 1-butanol to generate a rich organic extract with 1.6 g lactic acid per 100 ml of solvent. A 32 ml portion of the organic extract was contacted with 8 ml aqueous ammonia containing 3% (w/v) NH.sub.3, and mixed on a shaker for 30 min. After allowing the contents to settle for 1 hr, the phases were separated and lactic acid measured colorimetrically in the aqueous layer. The latter was found to contain 55.7 g/L lactic acid, which translates into a recovery of 87%. Another 32 ml portion of the lactic acid-loaded solvent was extracted with 8 ml of 4% (w/v) aqueous ammonia under conditions indicated above. The aqueous phase was found to have 60.9 g/L lactic acid, i.e. 95% recovery.

In a similar fashion, iso-amyl alcohol containing 1.58% (w/v) of lactic acid was obtained by extracting the fermentation broth used above an appropriate number of times with the alcohol. A 32 ml portion of this extract was back-extracted with 6% (w/v) aqueous ammonia at a volume ratio of 4:1 (30 min. mixing, 1 hr settling). The aqueous layer yielded a lactic acid concentration of 63.1 g/L, indicating an efficiency of over 98% for the back-extraction step.

EXAMPLE 12

A rich butanol extract, obtained from the extraction of a fermentation broth (also employed in Example 3), with 1-butanol and containing 18.1 g/L of lactic acid, was back-extracted with an aqueous suspension of calcium hydroxide. To 200 ml of organic extract was added a suspension of 2.5 g calcium hydroxide in 20 ml water, and the mixture was agitated mechanically in a flask for 1 hr. The aqueous phase along with any solids was separated after settling for 1 hr. A total of 20 flasks were similarly processed, thus completing the back-extraction of 4 L of rich butanol extract. The aqueous phases were combined, and the pH was brought down to 2-2.1 using concentrated sulfuric acid. Precipitated calcium sulfate was removed by filtration; the volume was 486 ml at this stage. Assay of lactic acid concentration yielded a value of 141.5 g/L in the filtrate, which corresponds to a back-extraction efficiency of 95%.

EXAMPLE 13

450 liters of fermentation broth containing 45 mg/ml of lactic acid of L/D ratio 96:4 was contacted with solvent continuously in a rotating disc contactor. The fermentation broth was fed from the top while the extractant was introduced at the bottom of the unit. After separation of phases, extract phase was continuously collected from the top and raffinate from the bottom of the extractor. Flow rates of the two phases were varied in the range of 10-50 Kg/hr. Under flow conditions of 10 Kg/hr of the fermentation broth and 30 Kg/hr of the solvent after attainment of steady state, concentration of lactic acid in the extractant was found to be 1.6 wt % indicating a recovery of over 95%.

EXAMPLE 14

1260Kg of solvent extract containing 1.6 wt % lactic acid obtained from the fermentation broth as described in example 9 was mixed with 26 Kg of lime dissolved/dispersed in 156 Kg of demineralized water in a 3000 litres continuous stirred tank reactor (CSTR) for a period of 2 hrs and reaction mixture was allowed to settle for 2 hrs for phase separation to occur. Bottom aqueous phase contained most of the lactic acid and the top regenerated solvent phase was taken for liquid-liquid extraction of lactic acid from a fresh broth. 204 Kg of aqueous lactate phase was obtained from the bottom of the reactor indicating over 99% recovery of lactic acid based on mass balance. The back aqueous extract thus obtained was acidified with concentrated sulphuric acid in a glass lined continuous stirred tank reactor (CSTR) to a pH of 2-2.5 for conversion of lactate to lactic acid. The acidified back extract was then centrifuged to remove the precipitated calcium sulphate. 30 Kg of DM water was used to wash the precipitate to recover entrained lactic acid. The filtrate containing lactic acid thus obtained was then passed through a column containing cation-exchange resin under the conditions of continuous column operation at rate of 3-5 bed volumes per hour. pH of the effluent from the column was found to decrease to a level of 1.5-2.0 after the treatment. Resin column was rinsed with two bed volumes of demineralised water to ensure recovery of entrapped lactic acid from the resin column for the recovery of residual lactic acid. 275 Kg of dark brown aqueous lactic acid solution thus obtained was concentrated in a packed glass-lined distillation column at 80-84° C. at a vacuum of 350 mm of Hg with a reflux ratio of 3:1 through a series of condensers. The water thus distilled (245 Kg) was used for the process of back extraction with another solvent extract. 30.5 Kg of aqueous lactic acid concentrate having 58 wt % lactic acid was obtained resulting into an overall lactic acid recovery of 88% from the process steps of back extraction to concentration.

EXAMPLE 15

82 g of aqueous lactic acid concentrate having lactic acid concentration of 66wt % obtained from the fermentation broth by liquid-liquid extraction, back-extraction with lime, acidification of lactate, resin treatment and concentration as described in above examples was taken in a 250 ml three necked round bottom glass flask fitted with facilities for the measurement of liquid temperature and nitrogen flushing through standard joints. The flask was connected to the two necked round bottom glass flask of capacity 100 ml as receiver through a short path distillation head and water/air condenser. A thermometer pocket was provided in the distillation head for the measurement of vapour temperature.

The reaction flask was kept in a rota-mantle for heating and mixing of the reaction mixture. Temperature was progressively increased to 140° C. under nitrogen flushing for the removal of water as distillate. Reaction mass was then cooled to 90° C. and 0.6 g of dibutyl tin oxide catalyst was then added to the reaction mixture under nitrogen blanketing. Temperature was then progressively increased in steps to 160° C. and vacuum was progressively increased from atmospheric to 60 mm of Hg in steps over a period of over 2 hrs for the removal of remaining water. After removal of water, reaction mixture was cooled to 90° C., water condenser was replaced by air condenser, receiver was cooled with ice and temperature was progressively increased in steps up to 290° C. and vacuum to 4 mm of Hg over a period of 5 hrs for the distillation of lactide. 40 g of crude lactide as product distillate was obtained resulting into a crude lactide yield of over 90% based on lactic acid.

EXAMPLE 16

83 g of aqueous lactic acid dark brown concentrate containing 75% concentration of lactic acid obtained from fermentation broth by liquid-liquid extraction, back extraction using ammonia, ion-exchange and concentration was employed for lactide formation using the experimental set-up as described in example 11. Temperature was increased gradually from ambient to 156° C. over a period of 3 hrs under nitrogen atmosphere for the removal of water. Reaction mixture was cooled to 85° C. and 1.6 g of catalyst, dibutyl tin oxide was added to the reaction mixture and temperature was gradually increased to 160° C. and vacuum was progressively increased from atmospheric to 40 mm of Hg over a period of 4 hrs. to remove remaining water from the reaction mixture. Reaction mixture was cooled again to 90° C. and lactide distillation was started by increasing temperature in steps to 235° C. and vacuum to 5 mm of Hg using short path air condenser and cooling the product receiver with dry ice for the lactide. 47 g of crude lactide distillate was collected in 4 hrs. leaving 7.5 g of residue in the reaction flask indicating a crude lactide yield of over 90%.

EXAMPLE 17

In an experiment on lactide formation, 42.5 Kg of dark colored viscous aqueous lactic acid concentrate containing 44.7% by weight lactic acid, prepared from fermentation broth through liquid-liquid extraction, back extraction, acidification, resin treatment and concentration was used as feed in a SS-316 autoclave reactor of working capacity 50 liters. The reactor was equipped with turbine type impeller for agitation, short path condenser, facilities for measuring liquid and vapour temperatures and port for nitrogen blanketing. A 20 litre three necked glass receiver for the product with bottom valve was connected to the reactor system through condenser. Reactor was jacketed for temperature control by hot oil circulation and vacuum was applied through one of the necks of the receiver using reflux condensers. After loading the feed to the reactor, temperature of the reaction mixture was slowly increased from ambient to 152° C. over a period of 10 hrs for the removal of water. Vapour temperature varied in the range of 100-108° C. during the period. 340 g of dibutyl tin oxide catalyst was then added, temperature was maintained in the range of 150-160° C. and vacuum was progressively increased from 600 to 60 mm of Hg over a period of 8 hrs for further removal of water. After removal of water, a vacuum of 10 mm of Hg was applied and temperature was progressively increased from 160 to 220° C. over a period of 14 hrs for the distillation of lactide. 13.4 Kg of crude lactide distillate was obtained resulting into a crude lactide yield of 87% based on lactic acid.

EXAMPLE 18

Crude lactide as prepared in example 11 from fermentation broth was purified by crystallization from ethyl acetate using crude lactide: ethyl acetate ratio of 5:3 by dissolving the lactide in a 100 ml round bottom flask fitted with reflux condenser, and the solution was allowed to cool at a temperature of 5° C. for 2-4 hrs for crystallization of lactide to occur. White lactide crystals of melting point 89° C. was obtained. This purified lactide on second recrystallization with ethyl acetate resulted in a purified lactide of melting point 97° C. comparable to that reported in literature. 2 g of this purified lactide was taken in a 100 ml round bottom flask and evacuated for 1 hr at 80° C. in an oil bath and 0.2 ml of 0.5% solution of tin octoate catalyst in toluene was then added and reaction mixture was evacuated for another 1 hr to remove the solvent. The system was sealed in vacuum and the temperature of the reaction mixture was slowly increased in steps to 180° C. with magnetic stirring and allowed to remain at 180° C. for 45 minutes for melt polymerization of lactide. Temperature was then lowered to 130° C. and the polymerization reaction was continued for another 12 hrs. The polymer thus produced was reprocessed by dissolution in chloroform, reprecipitation with methanol and drying to get 1.87 g of white product of specific solution viscosity 0.21 with 94% yield. DSC analysis of the polymer at a heating rate of 10° C./min gave three transitions characteristic of PLA at 55° C., 99° C. and 152° C. corresponding to glass transition, crystallization and melting of the polymer respectively.

EXAMPLE 19

2 g of purified lactide prepared following the procedure describe in example No. 14 was taken in 100 ml round bottom flask and was evacuated for 1 hr at 80° C. (oil bath). 0.4 ml of 0.5% solution of tin octoate in toluene was then added and the flask was further evacuated for 30 min for the removal of toluene. The reaction mixture was repeatedly flushed with nitrogen and the flask was sealed in the presence of nitrogen. The temperature of the reaction mixture was then raised slowly with magnetic stirring to 180° C. and melt polymerization was allowed to occur for 2 hrs at 180° C. followed by 150° C. for 4 hrs and 120° C. for 13 hrs. The GPC molecular weight of the reprocessed polymer was found to be 38,700 with a molecular weight distribution of 1.98. The DSC thermogram exhibited a melting endotherm of the polymer at 152° C. and a crystallization temperature of 108° C. on cooling.

EXAMPLE 20

Crude lactide prepared from lactic acid obtained from fermentation broth as described in example 12 was purified by two recrystallizations in ethyl acetate with lactid: ethyl acetate ratio of 5:3. Lactide was then filtered and recrystallized using toluene having a lactide: toluene ratio of 1:1. The melting point of thus purified lactide was found to be 99° C. 7.5 g of this lactide was taken in a round bottom flask and dried at 80° C. for 1 hr in vacuum of 5-10 mm of Hg. 0.6% tin octotate catalyst based on the lactide was then added and reaction mixture was dried for another 1 hr under vacuum. The flask was then sealed under vacuum and reaction mixture was polymerized at 180° C. for 35 minutes. A polymer of intrinsic viscosity 0.69 dL/g and GPC molecular weight of 78,000 was obtained with a yield of 90%.

EXAMPLE 21

Melt polymerization of 10 g of purified lactide having acidity of 0.01 wt % as lactic acid and moisture level of 180 ppm was carried out at 180° C. for 3 hrs. 0.2% tin octoate catalyst based on the weight of lactide was used. The experimental set up for melt polymerization was the same as described in example 16. Polymer of intrinsic viscosity 2.52 dL/g and GPC molecular weight of 2,35,000 was obtained with a polymer yield of 95%. DSC analysis of polymer sample gives a melting point of 170° C. and a heat of fusion 29 Kcal/mol.

EXAMPLE 22

Melt polymerization of purified lactide was carried out at 100 g per batch level. 100 g of lactide having acidity of 0.02% and moisture of 350 ppm was taken in a 250 ml round bottom flask. 0.056 wt % of tin octoate catalyst based on lactide was added and reaction mixture was evacuated for 2 hrs at 80° C. for the removal of moisture and toluene, used for preparing catalyst solution. The reaction mixture was sealed under vacuum and temperature was increased to 180° C. and maintain for 1 hr for melt polymerization to occur. Polymer of GPC molecular weight 2,13,000, and dispersity 2.12 was obtained with a conversion of 85%.

EXAMPLE 23

1.3 Kg of purified lactide was melt polymerized in presence of 0.056% tin octotate catalyst in 5 Kg Paar reactor equipped with mechanical agitation. The acid value of the lactide was 0.25%. Lactide was dried at 75-85° C. for 4 hrs under vacuum level of 20-30 mm of Hg. The mixture was repeatedly purged with nitrogen and assembly was sealed under vacuum. The temperature of the reaction mixture was slowly raised under stirring to 180° C. and maintained for 1 hr. 1.1 Kg of polymer having specific viscosity of 0.77 and GPC molecular weight of 72,000 was obtained with a polymer yield of nearly 85%.

In view of the foregoing descriptions, it will become apparent to those skilled in the art that equivalent modifications thereof may be made without departing from the spirit and scope of this invention.

We claim:

1. A process for producing polylactic acid from fermentation of renewable agricultural feed stocks comprising molasses or cane bagasse employed as a starting material containing sugars with all other substances present in molasses and cane bagasse, together with a nitrogen source selected from corn steep liquor, and autoclaved yeast paste, the process comprising the steps of;
   i) preparing a fermentation medium having molasses as a carbon source;
   ii) fermenting said fermentation medium;
   iii) extracting lactic acid from said fermentation medium using organic solvent and back extracting into the aqueous phase using hydroxide of ammonia, alkali or alkaline earth metal;
   iv) purifying said lactic acid solely with cation exchange resin, and concentrating said purified lactic acid;
   v) preparing lactide from said lactic acid;
   vi) polymerizing said lactide to form said polylactic acid; wherein
   vii) said renewable agricultural feed stock is cane molasses containing about 40% to about 50% (w/w) fermentable sugar; and
   viii) said renewal agricultural feed stock comprises cane bagasse, and including preparing said cane bagasse by hydrolyzing said bagasse particles with dilute acid for 30-90 min at 120° C. and treating said bagasse with 1-5% (w/v) alkali at 120° C. to 150° C. for a period of about 15 to about 90 minutes for delignification.

2. The process of claim 1, wherein said renewable agricultural feedstocks may be edible or non-edible.

3. The process of claim 1, wherein said renewable agricultural feed stock is cane molasses containing about 40% to about 50% (w/w) fermentable sugars.

4. The process of claim 1, wherein said molasses is adjusted to a fermentable sugar concentration of about 70g/L.

5. The process of claim 4, wherein the molasses is centrifuged to remove suspended materials and diluted with water to produce a fermentable sugar concentration of about 7% to about 10%.

6. The process of claim 5, further comprising a step of supplementing the molasses solution with about 2% to about 5% of said corn steep liquor and said autoclaved yeast paste.

7. The process of claim 1, wherein said fermenting step is carried out under anaerobic/microaerophilic conditions.

8. The process of claim 7, wherein said fermentation under anacrobic/microacrophilic conditions are carried out by microbe selected from the group consisting of *Lactobacillus, Streptococcus, Bacillus* and *Rhizopus*.

9. The process of claim 8, wherein said *lactobacillus* is selected from the group consisting of *L. delbrueckii, L. rhamnosus, L. helveticus, L. casei, L. plantarum, L. bulgaricus, L. amylovorans* and *L. lactis*.

10. The process of claim 1, wherein said fermenting step further comprises a step for adjusting and maintaining the pH of fermentation medium to between about 5.0 and about 6.0, thereby avoiding growth retardation of the microbe.

11. The process of claim 7, wherein said fermenting step is a continuous process or a fed batch fermentation process.

12. The process of claim 10, wherein said step of adjusting said pH of said fermentation medium is accomplished by employing a neutralizing agent selected from the group consisting of alkali, carbonates and ammonia.

13. The process of claim 1, wherein the lactic acid produced in the fermentation medium is extracted using organic solvents.

14. The process of claim 13, wherein said extracting step employs organic solvents selected from the group consisting of isoamyl alcohol, butanol, cyclohexanone and methyl acetate.

15. The process of claim 1, wherein said extracting step further comprises employing a solvent for separating said lactic acid from a fermentation medium at ambient temperature.

16. The process of claim 14, wherein said solvent is an alcohol or an ester.

17. The process of claim 13, wherein said process has an extraction efficiency of over 90%.

18. The process of claim 1, wherein said extracting step is not energy intensive.

19. The process of claim 1, wherein the extracted lactic acid is back extracted into aqueous phase, purified and concentrated.

20. The process of claim 19, wherein said step of back extraction of the lactic acid into aqueous phase from organic solvent is achieved using hydroxide of alkali or alkaline earth metals.

21. The process of claim 20, wherein the back extracted lactic acid in the aqueous phase is acidified using concentrated sulphuric acid to a pH ranging between 2-2.5.

22. The process of claim 1, wherein the purification involves passing the back extracted lactic acid through a cation exchange resin without elution by alkali.

23. The process of claim 22, wherein the purified lactic acid is concentrated in a packed glass lined distillation column.

24. The process of claim 23, wherein the concentrated lactic acid is converted into lactide in a reactor at a vapour temperature between about 120° C. and about 155° C. with a corresponding liquid temperature of about 180° C. to about 225° C.

25. The process of claim 24, wherein the conversion of lactic acid to lactide is carried out under a vacuum of about 5 to about 30 mm of Hg and combines prepolymerization and lactide formation into a single operation.

26. The process of claim 1, wherein the purification of lactide comprises a step of crystallization using organic solvents.

27. The process of claim 26, wherein the purified lactide is polymerized to give polylactic acid.

* * * * *